US007282083B2

(12) United States Patent
Rudkevich

(10) Patent No.: US 7,282,083 B2
(45) Date of Patent: Oct. 16, 2007

(54) METHODS, SYSTEMS, AND USES FOR CALIXARENES

(75) Inventor: Dmitry M. Rudkevich, Mansfield, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 317 days.

(21) Appl. No.: 10/643,160

(22) Filed: Aug. 18, 2003

(65) Prior Publication Data

US 2005/0063861 A1    Mar. 24, 2005

(51) Int. Cl.
    *B01D 53/04*    (2006.01)
(52) U.S. Cl. .................... 95/128; 95/129; 96/108; 204/416; 359/321; 422/82.05; 436/164
(58) Field of Classification Search ............ 95/128, 95/129; 96/108, 118; 210/634, 638, 644, 210/660, 681; 204/400, 415–420, 424; 359/321, 359/320; 422/82.05, 82.06, 82.03; 436/164, 436/165, 171, 103–118; 252/500, 502.1, 252/521.6; 385/16, 19
    See application file for complete search history.

(56) References Cited

U.S. PATENT DOCUMENTS

| 2,544,214 | A | * | 3/1951 | Berg ..................... 96/126 |
| 4,249,904 | A | * | 2/1981 | Rounbehler et al. ........ 436/178 |
| 5,132,345 | A | | 7/1992 | Harris et al. |
| 5,434,208 | A | * | 7/1995 | Batelaan et al. ............ 524/288 |
| 5,489,612 | A | | 2/1996 | Atwood et al. |
| 5,561,030 | A | * | 10/1996 | Holdcroft et al. ........... 430/311 |
| 6,136,071 | A | * | 10/2000 | Lamartine et al. ............ 95/128 |
| 6,400,880 | B1 | | 6/2002 | Hebert et al. |
| 6,605,236 | B1 | * | 8/2003 | Smith et al. ................ 252/500 |

OTHER PUBLICATIONS

Internet Publication: "Calixarenes, chemical chameleons", Erik van Dienst et al., Pure & Applied Chem., vol. 65, No. 3, pp. 387-392, Printed in Great Britain in 1993.*
Internet Publication: "Calixarenes, chemical chameleons", Erik van Dienst et al., Pure & Applied Chem., vol. 65, No. 3, pp. 387-392, Printed in Great Britain in 1993, downloaded from the Internet Nov. 14, 2005.*
S.V. Rosokha, et al.; *Molecular Recognition of $NO/NO^+$ via Multicenter (Charge-Transfer) Binding to Bridged Diarene Donors, Effect of Structure on the Optical Transitions and Complexation Thermodynamics*; J. Org. Chem. 2003, vol. 68; pp. 3947-3957.
S.V. Rosokha et al.; *Noval Arene Receptors as Nitric Oxide (NO) Sensors*; J. Am. Chem. Soc. 2002; vol. 124; pp. 5620-5621.
G.V. Zyryanov, et al.; *Sensing and Fixation of $NO_2/N_2O_4$ by Calix [4] Arenes*; J.Am. Chem. Soc. 2003; vol. 125; pp. 2997-3007.
G. V. Zyryanov, et al.; *Supramolecular Fixation of $NO_2$ with Calix [4] Arenes*; Chem. Commun. 2002; pp. 2792-2793.

* cited by examiner

*Primary Examiner*—Joseph Drodge
(74) *Attorney, Agent, or Firm*—Gardere Wynne Sewell LLP

(57) ABSTRACT

A method of identifying, detecting and/or chemically using $NO_X$ compounds is provided, wherein calixarene complexes are exposed to a nitrogen-oxide gas containing samples and form calixarene-nitrosonium complexes that are readily identified and detectable. Importantly, the process of forming one or more calixarene-nitrosonium ($NO^+$) complexes is reversible. The calixarene-nitrosonium complexes dissociate upon decoloration enabling the parent calixarenes to be recovered.

23 Claims, No Drawings

METHODS, SYSTEMS, AND USES FOR CALIXARENES

BACKGROUND OF THE INVENTION

The present invention relates to the general field of chemical sensing, and more particularly to calixarene compositions, devices and methods of use for identifying and detecting the presence of nitrogen oxide compounds in gas/vapor or liquid mixture.

Nitrogen oxide compounds, the so-called $NO_X$ gases—a collective term that refers to the family of oxides of nitrogen—are toxic atmospheric pollutants derived generally from fossil fuel combustion, power plants, and large-scale industrial processes. $NO_X$ are involved in the formation of ground-level ozone, participate in global warming, and also form toxic chemicals, nitrate particles and acid rain/aerosols. In addition, $NO_X$ are active components in various harmful nitrosation processes in biological tissues. Free radical NO rapidly reacts with oxygen, producing $N_2O_3$ (e.g., $NO.NO_2$) and $NO_2/N_2O_4$ that are powerful nitrosating agents, both in the gas phase and in solution.

The pathophysiologic significance of $NO_X$ derives from their ability to generate mutagenic nitrosopeptides and diazopeptides, to produce carcinogenic nitrosoamines, and to nitrosate and deaminate DNA nucleobases. According to The United States Environmental Protection Agency, national emissions of $NO_X$ have increased over the past 20 years by 4% and continue to rise. With the increase in $NO_2$ circulation in the atmosphere, there remains a need to not only systematically monitor nitrogen levels in the atmosphere, and to develop improved methods of fixation and utilization of nitrogen oxide compounds.

The present invention addresses many of the needs mentioned above as well as other objectives that will be appreciated by those skilled in the art.

SUMMARY OF THE INVENTION

The present invention solves many problems associated with current increases in $NO_x$ levels in the atmosphere. The present invention provides new and improved methods of detecting and identifying of $NO_X$ compounds, provides new and improved uses of these compounds as well as methods for storage of $NO_X$ compounds. New and improved compounds for use in such applications are also provided.

In accordance with one aspect of the present invention, a method of and device for identifying, detecting and/or chemically utilizing $NO_X$ compounds is provided, wherein simple calixarenes, such as calix[4]arenes (e.g., tetra-O-alkylated calix[4]arenas) are exposed to nitrogen oxides capable of producing nitrosonium ions (i.e. $NO^+$) and form calixarene-nitrosonium complexes that are readily identified. Importantly, the process of forming one or more calixarene-nitrosonium complexes is reversible. In addition, the calixarene-nitrosonium decolor with the addition of anything that reacts with the nitrosonium ion (e.g., water, alcohol) enabling the parent calixarenes (e.g., calix[4]arenes) to be recovered.

In accordance with another aspect of the present invention, a method of and device for attaching functionalized calix[4]arenes to a solid support (e.g., silica gel) is provided resulting in a solid material capable of identification, detection and/or entrapment of $NO_X$ compounds. As such nitrogen oxide compounds may be readily purified by means of the present invention.

Further, in accordance with the present invention, a method of and device for using calixarene-nitrosonium complexes is provided for the transfer of $NO^+$ for nitrosation reactions. As such, novel nitrogen oxides storing materials are also provided.

An advantage of the present invention is that it provides a new and improved charge-transfer interaction for $NO_X$ compounds ($NO_X$) allowing the compounds to be readily detected in the presence of other gases, including $H_2O$, $O_2$, HCl, $SO_X$, $NH_3$, and even NO. In addition, the $NO_X$ compounds and complexes formed with the present invention are vehicles for nitrosonium transfer and for encapsulated nitrosating reagents. The complexes also serve as nitrogen oxide (e.g., $NO_2/NO_X$) detection, sensing materials.

Those skilled in the art will further appreciate the above-mentioned advantages and superior features of the invention, together with other important aspects thereof upon reading the detailed description that follows in conjunction with the drawings.

DETAILED DESCRIPTION OF THE INVENTION

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

Nitrogen oxide compounds, also referred to as $NO_X$ gases are toxic atmospheric compounds as well as pathophysiologic compounds. As used herein, $NO_X$ refers to any mixture of oxides of nitrogen capable of generating a nitrosonium ion. One of the most prevalent of these compounds is $NO_2$, a paramagnetic gas since it has an unpaired electron on the nitrogen. It has an intense brown-orange color. When reacting with itself, it forms a colorless dimer, dinitrogen tetroxide ($N_2O_4$). For $N_2O_4$, there is a very weak N—N bond and, at higher temperatures, the gas rapidly dissociates back to $NO_2$. The position of equilibrium between the two compounds ($N_2O_4$ and $NO_2$) and the color of the system varies with temperature. Below −21 degrees Centigrade, only pure, solid $N_2O_4$ is present. Above 140 degrees Centigrade the system is 100% $NO_2$. This dynamic interconversion between $NO_2$ and $N_2O_4$ makes it impossible to study either of species alone. Of particular importance for mammals is that $N_2O_4$ may disproportionate to ionic $NO^+$ $NO_3^-$.

Calix[4]arenes are building block-like molecules and have been used in the construction of molecular containers (e.g., cavitands, (hemi)carcerands, and capsules). Cone-shaped calix[4]arenes are about 4 Å deep and about 7 Å in diameter at the upper rim. Tetra-O-alkylated cone calix[4] arenes exist in the pinched $C_{2v}$ symmetrical conformation, with two opposite aromatic rings almost parallel and situated about 5 Å apart, and two others flattened. This conformation is more preferable than the perfect cone $C_{4v}$ conformation. Usually, the interconversion between two $C_{2v}$ structures is fast on the NMR time scale. Calix[4]arenes in a 1,3-alternate conformation are much more rigid and possess a cylindrical inner tunnel, defined by two cofacial pairs of aromatic rings oriented orthogonal along the cavity axis. According to a number of X-ray studies, this tunnel is about 5-6 Å in diameter.

Complexes of calix[4]arenes with neutral molecules are weak. The cavities are obviously too small and they lack additional binding sites. In most of the crystal structures of the inclusion complexes of calixarenes, the guest molecule (i.e., the molecule that forms a complex with a calixarene) is positioned not inside, but roughly above the plane defined by the upper carbon atoms of the cyclic polyaromatic skeleton. Cations are known to interact with more strength with a calixarene π-surface. Ammonium ions and metal cations have been found to complex within the cone-shaped cavities. 1,3-Alternates, functionalized with appropriate binding sites on the phenol oxygens, bind metal cations (e.g., $Na^+$, $K^+$, and $Ag^+$) both with "hard" oxygens and "soft" π-basic aromatic rings.

The present invention has found that interactions between calix[4]arenes and nitrogen oxide compounds leads to strong calixarene-nitrosonium complexes and shows the host-guest complexes formed upon interaction between $NO_x$ and simple calix[4]arenes. In fact, calixarene complexes of the present invention are identified by: (1) an ability to react with $NO_x$ to form stable nitrosonium ($NO^+$) complexes; (2) identification and detection (e.g., colorization) of the calixarene-$NO^+$ complexes; and (3) dissociation of the identified calixarene-$NO^+$ complexes (e.g., decoloration of the complex via anything that reacts with the nitrosonium ion, such as water or alcohol, as examples). Importantly, the calixarene-$NO^+$ complexes may be used for the transfer of $NO^+$ compounds, nitrosation reactions, $NO_X$ identification, $NO_X$ detection, and $NO_X$ sensing, as well as serving as supramolecular $NO^+$ storing materials.

General Procedures

General methods of the present invention are described here and include those in Zyryanov G., et al. JACS. 2003; 125:2997-3007 (incorporated herein by reference). Melting Points were determined on a Mel-Temp apparatus (Laboratory Devices, Inc.) and a Buchi apparatus. $^1H$ and $^{13}C$ NMR spectra were recorded in $CDCl_3$ at 295± degrees Centigrade, unless stated otherwise, on JEOL Eclipse 500 MHz spectrometer. Chemical shifts were measured relative to residual non-deuterated solvent resonances. FTIR spectra were recorded on a Bruker Vector 22 FTIR spectrometer. UV-vis spectra were measured on a JASCO V-530 spectrophotometer. Matrix-assisted laser desorption/ionization mass spectrometry (MALDI-TOF) was performed on a Bruker BiFLEX I linear time-of-flight mass spectrometer operated in delayed extraction mode. Elemental analysis was performed on a Perkin-Elmer 2400 CHN analyzer. For column chromatography, Silica Gel 60 Å (Sorbent Technologies, Inc.; 200-425 mesh) was used. All experiments with moisture- or air-sensitive compounds were run in freshly distilled, anhydrous solvents under a dried nitrogen atmosphere. Molecular modeling was performed generally using MacroModel 7.1.

Parent tetrahydroxycalix[4]arenes were prepared according to procedures known to one of ordinary skill in the art (see e.g., Gutsche, C. D., Iqbal, M. *Org. Synth.* 1990, Vol. 68, pp. 234-237). $NO_2/N_2O_4$ was generated from copper and concentrated $HNO_3$ or sodium nitrate and concentrated $H_2SO_4$.

Example for Preparing 25,26,27,28-Tetra (n-hexyloxy)calix[4]arene-1,3-alternate (compound 2)

To a suspension of 25,27,26,28-tetrahydroxycalix[4]arene (about 4.24 g, 0.01 mol) and $K_2CO_3$ (about 4.2 g, 0.03 mol) in MeCN (about 200 mL) n-hexylbromide (about 4.2 mL, 0.03 mol) was added, and the reaction mixture was refluxed under nitrogen for about 48 hours. The precipitate was filtered off, and the solution evaporated to dryness. The residue was redissolved in $CH_2Cl_2$ (about 200 mL), and the solution washed with water (3×150 mL) and dried over $MgSO_4$. After evaporation, the solid residue was treated with MeOH (about 200 mL) to yield pure 25,27-bis(n-hehyloxy)-26,28-hydroxycalix[4]arene as a white solid (5.0 g, 84%). $^1H$ NMR results: δ 8.23 (bs, 2H), 7.06 (d, J=8 Hz, 4H), 6.91 (d, J=8 Hz, 4H), 6.73 (t, J=8 Hz, 2H), 6.65 (t, J=8 Hz, 2H), 4.32 (d, J=13 Hz, 4H), 4.00 (t, J=7 Hz, 4H), 3.37 (d, J=13 Hz, 4H), 2.1-2.0 (m, 4H), 1.75-1.7 (m, 4H), 1.45-1.4 (m, 8H), 0.95 (t, J=7 Hz, 6H).

To a suspension of 25,27-bis(n-hehyloxy)-26,28-hydroxycalix[4]arene (about 5.92 g, 0.01 mol) and $Cs_2CO_3$ (about 50 g, 0.15 mol) in MeCN (about 300 mL) n-hexylbromide (about 5.74 mL, 0.04 mol) was added, and the reaction mixture was refluxed under nitrogen for about 48 hours. After cooling, the precipitate was filtered off and treated with a mixture of water (about 100 mL) and $CH_2Cl_2$ (about 100 mL). The organic layer was separated, washed with water (2×100 mL), dried over $MgSO_4$, and evaporated. The residue was recrystallized from MeOH—$CHCl_3$, 10:1 to give pure compound 2 (3.50 g, 46%). Melting Point: 119 degrees Centigrade. $^1H$ NMR results were: δ 6.92 (d, J=7.5 Hz, 8H), 6.68 (t, J=7.5 Hz, 4H), 3.62 (s, 8H), 3.54 (t, J=7.5 Hz, 8H), 1.89 (m, 8H), 1.35 (m, 24H), 0.85 (t, J=7 Hz, 12H). MALDI-TOF MS, m/z 783.9 ([M+$Na^+$], calculated for $C_{52}H_{72}O_4$ 783.9). Anal. calculated for $C_{52}H_{72}O_4$: C, 82.06; H, 9.53. Found: C, 81.61; H, 9.58.

Example for Preparing 5,11,17,23-Tetrabromo-25, 26,27,28-tetrakis(n-hexyloxy)calix[4]arene-1,3-alternate (compound 3)

N-Bromosuccinimide (about 3.0 g, 0.017 mol) was added to a suspension of calixarene 2 (about 2.0 g, 2.6 mmol) in acetone (about 500 mL), and the mixture was stirred at room temperature for about 48 hours and exposed to the laboratory light. The formed solid was filtered off, washed with acetone (about 2×100 mL) and used in the next step without further purification. Yield 1.5 g (53%). $^1H$ NMR results were: δ 7.12 (s, 8H), 3.56 (s, 8H), 3.52 (t, J=7.5 Hz, 8H), 1.6-1.4 (m, 8H), 1.4-1.3 (m, 24H), 0.93 (t, J=7 Hz, 12H).

Example for Preparing 5,11,17,23-Tethydroxy-25, 26,27,28-tetrakis(n-hexyloxy) calix[4]arene-1,3-alternate (compound 4)

To a solution of tetrabromo derivative compound 3 (about 0.9 g, 0.83 mmol) in freshly distilled over Na and oxygen-free THF (about 150 mL) n-BuLi (about 30 mL of 2M solution in pentane, 60 mmol) was added at −78 degrees Centigrade, and the mixture was stirred at this temperature for about 75 minutes. Trimethyl borate (about 14 mL, 145 mmol) was then added at −78 degrees Centigrade, and the mixture was allowed to warm to room temperature. After about 5 hours, the reaction mixture was cooled down again to −78 degrees Centigrade, and $H_2O_2$ (about 15 mL of 30% aqueous solution) and NaOH (about 35 mL of 3N aqueous solution) was added. The resulting solution was stirred overnight at room temperature, after which the precipitate was filtered off. The mother liquor was cooled to 0 degrees Centigrade and treated with $NaS_2O_3$ (about 25 g), after which the mixture was filtered and the filtrate was concentrated in vacuo. The residue was treated with about 5% aqueous HCl (100 mL), and the colorless precipitate of compound 4 was filtered off and washed with MeOH (about 50 mL). Yield 0.274 g (40%). Melting Point: 230 degrees Centigrade. $^1$H NMR results were (DMSO-d$_6$): δ 8.39 (bs, 4H), 6.34 (s, 8H), 3.50 (s, 8H), 3.02 (t, J=7.5 Hz, 8H), 1.3-1.25 (m, 8H), 1.25-1.1 (m, 16H), 1.1-1.0 (m, 8H), 0.87 (t, J=7 Hz, 12H). MALDI-TOF MS, m/z 847 ([M+Na$^+$], calculated for C$_{52}$H$_{72}$O$_8$ 847).

Example for Preparing 5,11,17,23,25,26,27,28-Octa (n-hexyloxy)calix[4]arene-1,3-alternate (compound 5)

To a suspension of compound 4 (about 0.3 g, 0.36 mmol) and NaH [about 0.15 g of about 60% (wt.) suspension in mineral oil, 3.6 mmol] in freshly distilled DMF (about 50 mL) n-hexylbromide (about 0.46 mL, 3.2 mmol) was added, and the reaction mixture was stirred at about 70 degrees Centigrade under nitrogen for about 24 hours. The precipitate was filtered off, and the mother liquor was treated with a mixture of crushed ice (about 50 g), water (about 50 mL) and CH$_2$Cl$_2$ (about 100 mL). The organic layer was separated, washed with water (2×100 mL), dried over MgSO$_4$ and evaporated. The residue was recrystallized from MeOH—CHCl$_3$, 10:1 to yield calixarene compound 5 (0.35 g, 85%). Melting Point: 11 degrees Centigrade. $^1$H NMR results were: δ 6.55 (s, 8H), 3.83 (t, J=7 Hz, 8H), 3.62 (s, 8H), 3.35 (t, J=7 Hz, 8H), 1.7 (m, 16H), 1.4-1.2 (m, 48H), 0.89 (t, J=7 Hz, 24H). $^{13}$C NMR results were: δ 153.6, 150.7, 134.4, 115.2, 71.6, 68.1, 37.8, 32.3, 31.8, 29.8, 26.0, 25.9, 22.9, 22.7, 14.3, 14.1; MALDI-TOF MS, m/z 1182 ([M+Na$^+$], calculated for C$_{76}$H$_{120}$O$_8$ 1183).

Example for Preparing Tetrakis(O-n-hexyloxy)cyclophane (compound 6)

NaH (about 0.11 g of about 60% suspension in mineral oil, 2.7 mmol) was added to the solution of Pappalardo's cyclophane (about 0.2 g, 0.34 mmol prepared using methods known in the art) in freshly distilled DMF (about 20 mL), and the mixture was stirred under nitrogen for about 30 minutes. n-Hexylbromide (about 0.3 mL, 2.04 mmol) was then added, and the reaction mixture was stirred at about 70 degrees Centigrade for 3 days. The precipitate was collected and dissolved in CH$_2$Cl$_2$ (about 20 mL). The solution washed with water (3×20 mL), dried over MgSO$_4$ and evaporated. The residue was recrystallised from MeOH—CHCl$_3$ to afford compound 6 as a white powder. Yield 0.157 g (50%). $^1$H NMR results were: δ 3.89 (s, 8H), 3.58 (t, J=7 Hz, 8H), 2.30 (s, 24H), 1.8-1.7 (m, 8H), 1.6-1.5 (m, 16H), 1.4-1.35 (m, 8H), 1.07 (s, 12H), 0.91 (t, J=7 Hz, 12H). $^{13}$C NMR results were: δ 153.9, 138.4, 131.4, 126.7, 73.2, 32.8, 32.0, 30.4, 26.0, 22.8, 17.7, 14.2, 13.7. Anal. calculated for C$_{64}$H$_{96}$O$_4$: C, 82.70; H, 10.41. Found: C, 82.37; H, 10.25.

Example for Preparing Calix[4]arene-nitrosonium Complexes

In one example, stock solutions of NO$_2$ were freshly prepared upon bubbling through CHCl$_3$; the gas concentration was determined gravimetrically. In a typical procedure, a solution of calixarene compound 1 (about 1 equivalent) in dry, freshly distilled CHCl$_3$ was mixed with the stock solution of NO$_2$ (about 3 equivalent) in CHCl$_3$ and SnCl$_4$ (about 1.5 eq) at room temperature. After 1 hour, complex 7 was precipitated upon addition of hexane, filtered off, washed with hexane (about 2 times), and dried in vacuo. $^1$H NMR results were: δ 6.99 (s, 8H), 4.39 (d, J=13 Hz, 4H), 4.02 (t, J=7.5 Hz, 8H), 3.44 (d, J=13 Hz, 4H), 2.0-1.9 (m, 8H), 1.5-1.3 (m, 24H), 0.93 (t, J=7 Hz, 12H); UV-vis (CHCl$_3$): λ$_{max}$ 563; FTIR (CDCl$_3$): ν 1923 (NO-11461, 1298, 1047 (NO$_3$$^-$); Anal. calculated for C$_{68}$H$_{104}$O$_4$.NO$^+$ NO$_3$$^-$.1.8SnCl$_4$: C, 52.81; N, 1.81; H, 6.78. Found: C, 52.60; N, 1.67; H, 7.55. Complex 8 was obtained analogously and $^1$H NMR results were: δ 7.17 (t, J=7.5 Hz, 4H), 7.08 (d, J=7.5 Hz, 8H), 3.87 (t, J=7.5 Hz, 8H), 3.60 (s, 8H), 1.9-1.8 (m, 8H), 1.4-1.3 (m, 24H), 0.93 (t, J=7 Hz, 12H); UV-vis (CHCl$_3$): λ$_{max}$ 524 nm; FTIR (CDCl$_3$): ν 1955 (NO$^-$), 1438, 1246 1901, (NO$_3$$^-$). Anal. calculated for C$_{52}$H$_{72}$O$_4$.NO$^+$ NO$_3$$^-$.1.5SnCl$_4$: C, 50.21; N, 2.25; H, 5.83. Found: C, 50.23; N, 1.82; H, 5.99. Complex 9 is generally not prepared using this protocol; because, only dealkylation/oxidation products were detected. For spectroscopic characterization, complex 9 was generated in the exchange experiment between nitrosonium complex 8 and free calixarene compound 5.

In another example, calix[4]arene-nitrosonium complexes were obtained upon mixing compound 1, 2 or 5 with an excess NO$^+$SbF$_6$$^-$ in dry CHCl$_3$. Complexes 1.NO$^+$SbF$_6$$^-$ and 2.NO$^+$SbF$_6$$^-$ formed within about 20 hours. The UV-vis, FTIR and $^1$H NMR spectra were identical with the respective complexes 7 and 8. Complex 5.NO$^+$SbF$_6$$^-$ formed immediately upon mixing. $^1$H NMR results were: δ 6.54 (s, 8H), 3.93 (t, J=7.5 Hz, 8H), 3.76 (t, J=7.5 Hz, 8H), 3.44 (s, 8H), 1.8-1.75 (m, 8H), 1.9-1.8 (m, 8H), 1.5-1.2 (m, 48H), 0.95 (t, J=7 Hz, 12H), 0.89 (t, J=7.5 Hz, 12H); UV-vis (CHCl$_3$): λ$_{max}$ 600; FTIR (CDCl$_3$): ν (NO$^+$) 1876.

Example for Preparing 25-Hydroxy-26,27,28-trihexyloxy-p-tert-butylcalix[4]arene (compound 10)

A mixture of 25,26,27,28-tetrahydroxy-p-tert-butylcalix[4]arene (about 4.0 g, 6.2 mmol), freshly distilled anhydrous DMF (about 80 mL), Ba(OH)$_2$.8H$_2$O (about 6.8 g, 21.6 mmol), and BaO (about 6.36 g, 41.5 mmol) were stirred at room temperature for 15 minutes. n-Hexylbromide (about 21 mL, 184 mmol) was added, and the suspension was stirred at room temperature for another about 12 hours. The mixture was diluted with water (about 100 mL), and the product was extracted with CH$_2$Cl$_2$ (3×100 mL). The organic layer was washed with water (2×100 mL), dried over Na$_2$SO$_4$ and evaporated under reduced pressure. The residue was recrystallized from MeOH to give pure compound 10 as a white solid. Yield 69%; Melting Point: 134-136 degrees Centigrade. $^1$H NMR results were: δ 7.11 (s, 2H), 7.03 (s, 2H), 6.51 (d, J=2.3 Hz, 2H), 6.49 (d, J=2.3 Hz, 2H), 5.72 (s, 1H), 4.36 (d, J=13 Hz, 2H), 4.32 (d, J=13 Hz, 2H), 3.89 (t, J=8 Hz, 2H), 3.78 (t, J=8 Hz, 4H), 3.22 (d, J=13 Hz, 2H), 3.16 (d, J=13 Hz, 2H), 2.3-2.2 (m, 2H), 2.0-1.8 (m, 4H), 1.4-1.3 (m, 18H), 1.32 (s, 9H), 1.31 (s, 9H), 0.92 (t, J=7 Hz, 3H), 0.90 (m, 6H), 0.81 (s, 18H).

Example for Preparing 25-[(Ethoxycarbonyl)methoxy]-26,27,28-trihexyloxy-p-tert-butylcalix[4]arene (11)

A mixture of calix[4]arene compound 10 (about 5.0 g, 5.6 mmol) and Na$_2$CO$_3$ (about 10.0 g, 94 mmol) in CH$_3$CN (about 150 mL) was refluxed for about 15 minutes, after which ethyl bromoacetate (about 10 mL, 90 mmol) was added, and the reflux continued for 12 hours. The inorganic salts were filtered, and the solvent was evaporated. The residue was dissolved in CH$_2$Cl$_2$ (about 100 mL) and washed with water (3×50 mL). The solvent was evaporated, and the product was recrystallized from MeOH. Yield 89%; Melting Point: 121-123 degrees Centigrade. $^1$H NMR results were: δ 6.91 (s, 2H), 6.90 (s, 2H), 6.63 (d, J=2 Hz, 2H), 6.61

(d, J=2 Hz, 2H), 4.86 (s, 2H), 4.66 (d, J=12.5 Hz, 2H), 4.38 (d, J=12.5 Hz, 2H), 4.18 (q, J=7 Hz, 2H), 3.83 (t, J=8 Hz, 4H), 3.75 (t, J=8H, 2H), 3.15 (d, J=12.5 Hz, 2H), 3.10 (d, J=12.5 Hz, 2H), 2.2-2.1 (m, 2H), 2.0-1.9 (m, 4H), 1.4-1.3 (m, 18H), 1.27 (t, J=7 Hz, 3H), 1.18 (s, 9H), 1.17 (s, 9H), 0.96 (s, 18H), 0.9-0.8 (m, 9H).

Example for Preparing 25-(Carbomethoxy)-26,27, 28-trihexyloxy-p-tert-butylcalix[4]arene (compound 12)

A mixture of compound 11 (about 2.0 g 2 nmol), THF—$H_2O$, about 5:1 (100 mL) and KOH (about 1.0 g, 17.8 mmol) was refluxed for about 12 hours. The pH was adjusted to about 4 with aqueous 2 M HCl. The product was extracted with $CH_2Cl_2$ (2×50 mL), and the organic layer was dried over $Na_2SO_4$ and evaporated to give compound 12 as a white solid. Yield >95%; Melting Point: 136-137 degrees Centigrade. $^1$H NMR results were: δ 11.28 (s, 1H), 7.16 (s, 2H), 7.14 (s, 2H), 6.59 (d, J=2.5 Hz, 2H), 6.49 (d, J=2.5 Hz, 2H), 4.67 (s, 2H), 4.45 (d, J=12 Hz, 2H), 4.23 (d, J=12 Hz, 2H), 4.08 (t, J=7 Hz, 2H), 3.8-3.7 (m, 4H), 3.24 (d, J=12 Hz, 2H), 3.16 (d, J=12 Hz, 2H), 1.95-1.8 (m, 6H), 1.45-1.2 (m, 18H), 0.90 (t, J=7 Hz, 9H), 0.83 (s, 18H); MALDI-TOF MS, m/z 959.2 ($M^+$, calculated for $C_{64}H_{94}O_6$ 960.4). Anal. calculated for $C_{64}H_{94}O_6$: C, 80.12; H, 9.88. Found: C, 80.27; H, 9.88.

Example for Preparing N-Succinimide Ester of 25-(Carbomethoxy)-26,27,28-trihexyloxy-p-tert-butyl-calix[4]arene (compound 13)

A suspension of compound 12 (about 1.0 g, 1.05 mmol), N-hydroxy succinimide (about 1.0 g, 8.70 mmol), DCC (210 mg 1.05 mmol) and DMAP (about 40 mg, 0.32 mmol) in THF (about 50 mL) was stirred at room temperature for about 12 hours under nitrogen. After filtration, the solvent was evaporated, and the residue was redissolved in hexane (50 mL) and filtered again. The hexane solution was evaporated and the residue was purified by column chromatography (about $CH_2Cl_2$-hexane, 1:1) to afford compound 13 as a white solid. Yield 83%; Melting Point: 75-78 degrees Centigrade; $^1$H NMR results were: δ 6.95 (s, 2H), 6.92 (s, 2H), 6.62 (d, J=2.5 Hz, 2H), 6.56 (d, J=2.5 Hz, 2H), 5.28 (s, 2H), 4.56 (d, J=13 Hz, 2H), 4.41 (d, J=13 Hz, 2H), 3.89 (t, J=8 Hz, 2H), 3.79 (t, J=8 Hz, 2H), 3.75 (t, J=8 Hz, 2H), 3.18 (d, J=13 Hz, 2H), 3.12 (d, J=13 Hz, 2H), 2.82 (s, 4H), 2.15-2.1 (m, 2H), 1.95-1.85 (m, 4H), 1.45-1.35 (m, 18H), 1.20, 1.19 (2×s, 18H), 0.93 (s, 18H), 0.9-0.8 (m, 9H). Ester compound 13 appeared to be relatively unstable; attempts to obtain the MALDI-TOF and/or CHN analytical data failed. The structure of compound 13 was confirmed through its transformation to calixarene amide compound 14.

Example for Preparing 25-[(n-Octylcarbamoyl-methoxy)-26,27,28-trihexyloxy-p-tert-butylcalix[4]arene (compound 14)

To the solution of ester compound 13 (about 75 mg, 70 μmol) in THF (about 10 mL), n-octylamine (about 18 mg, 0.14 mmol) and $Et_3N$ (about 70 mg, 0.7 mmol) were added, and the reaction mixture was stirred at room temperature for about 12 hours. The precipitate was filtered off, and the solution was evaporated. The residue was redissolved in $CH_2Cl_2$ (about 20 mL), washed with 2 M aqueous HCl (2×5 mL) and water (about 5 mL), and dried over $Na_2SO_4$. The organic layer was then evaporated and the residue was recrystallized from $CH_3CN$ to afford compound 14 as a white solid. Yield 65%. $^1$H NMR results were: δ 8.43 (t, J=6 Hz, 1H), 6.99 (s, 2H), 6.97 (s, 2H), 6.57 (s, 4H), 4.71 (s, 2H), 4.38, 4.35 (2×d, J=13 Hz, 4H), 3.9-3.7 (2×m, 6H), 3.42 (dt, J=6 Hz, J=7 Hz, 2H), 3.23 (d, J=13 Hz, 2H), 3.14 (d, J=13 Hz, 2H), 2.0-1.8 (3×m, 8H), 1.5-1.3 (m, 30H), 1.25 (s, 9H), 1.23 (s, 9H), 0.93 (s, 18H), 0.95-0.85 (m, 12H). FTIR (KBr): ν 3346 (NH), 2964, 1680 (C=O), 1537, 1473. Anal. calculated for $C_{72}H_{111}NO_5 \cdot 0.5CH_3CN$: C, 80.35; H, 10.39; N, 1.93. Found: C 80.02; H, 10.09; N, 1.91. Compound 14 was also independently synthesized from the acid chloride of compound 12 (prepared with $SOCl_2$), n-octylamine and $Et_3N$ in $CHCl_3$.

Example for Preparing a Calix[4]arene Functionalized Silica Gel (15)

A suspension of ester compound 13 (about 100 mg, 95 μmol), 3-aminopropyl-functionalized silica gel (Aldrich) (about 226 mg, 155 μmol) and $Et_3N$ (about 92.9 mg, 0.92 mmol) in THF (50 mL) was stirred at room temperature for about 12 hours. The solid was filtered off, washed with $CH_2Cl_2$, MeOH, water, MeCN, and THF, and then dried under reduced pressure for about 3 days to provide a white powder. FTIR (KBr): ν 3383, 2960, 1650, 1556, 1477. Anal. Found for 3-aminopropyl silica gel (0.687 meq/g, $C_9H_{23}NO_3Si$): C, 7.42; H, 1.80; N, 1.91. Anal. Calcd for silica gel 15 (17% loading, 0.117 meq/g, $C_{73}H_{115}NO_8Si$): C, 15.43; H, 2.68; N, 1.82. Found: C, 15.34; H, 2.97; N, 1.70.

Example for Preparing N-Nitrosation of Amides by Calix[4]arene-Nitrosonium Complexes. [It is noted that N-Nitrosoamides are potential carcinogens and should be treated with extreme care.]

Complex 8 (about 1 equivalent) was added to the solution of amide AlkC(O)NHMe 16a-c (about 2-3 equivalents) in freshly distilled $CHCl_3$, and the reaction mixture was stirred at room temperature for about 5 hours. The solvent was evaporated, and the residue was analyzed by $^1$H NMR spectroscopy and further separated by preparative TLC. The spectral data for the obtained N-nitroso compounds AlkC(O)N(NO)Me 17a-c were identical with those independently obtained from AlkC(O)NHMe and $NO_2/N_2O_4$ or $NO^+SbF_6^-$, and similar to results observed by others. (See, e.g., Garcia, J., et al. J. Org. Chem. 1984, 49, pp. 3322-3327) For $CH_3(CH_2)_6C(O)NHCH_3$ (16b), $^1$H NMR results were: δ 6.13 (bs, 1H, NH), 2.73 (d, J=5 Hz, 3H, N—$CH_3$), 2.13 (t, J=7.5 Hz, 2H, C(O)$CH_2$), 1.6-1.5 (m, 2H, $CH_2$), 1.3-1.1 (m, 8H, $CH_2$), 0.83 (t, J=7.5 Hz, 3H, $CH_3$). For $CH_3(CH_2)_6C(O)N(NO)CH_3$ (17b), $^1$H NMR results were: δ 3.13 (t, J=8 Hz, 2H, C(O)$CH_2$), 3.03 (s, 3H, N(NO)—$CH_3$), 1.8-1.7 (m, 2H, $CH_2$), 1.4-1.2 (m, 8H, $CH_2$), 0.84 (t, J=7.5 Hz, 3H, $CH_3$).

General Procedures for Synthesis of Compounds and Complexes of the Present Invention.

Calix[4]arenes compounds 1 and 2, possessing a cone and a 1,3-alternate conformation, respectively, were synthesized through O-alkylation of the corresponding parent calix[4] arenes with n-hexylbromide (see SCHEME 1). In the synthesis of compound 1, NaH was employed as a base in hot DMF. The preparation of compound 2 may include the two-step alkylation of de-t-butylated calix[4]arene with n-hexyl bromide, using successively $K_2CO_3$ and then $Cs_2CO_3$ in boiling MeCN.

SCHEME 1

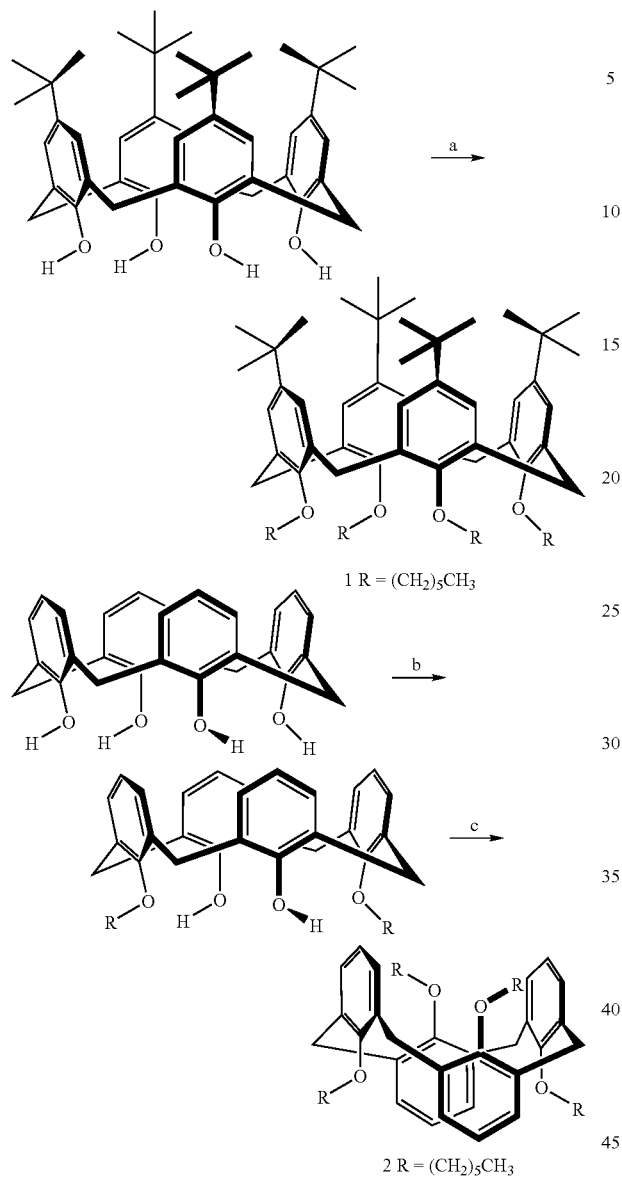

1 R = (CH$_2$)$_5$CH$_3$

2 R = (CH$_2$)$_5$CH$_3$ (a) n-hexyl bromide, NaH, DMF, 70 degrees Centigrade, 24 hours, 75% yield;
(b) n-hexyl bromide, K$_2$CO$_3$, MeCN, 80 degrees Centigrade, 48 hours, 84% yield;
(c) n-hexyl bromide, Cs$_2$CO$_3$, MeCN, 80 degrees Centigrade, 48 hours, 46% yield.

SCHEME 2

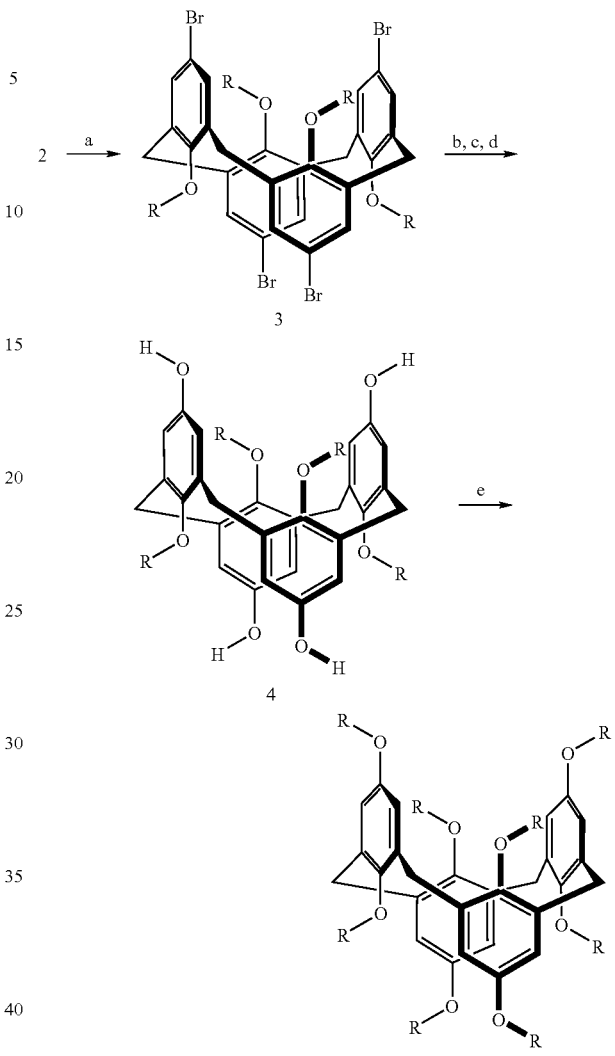

5 R = (CH$_2$)$_5$CH$_3$ (a) NBS, acetone, room temperature, 48 hours, 53% yield;
(b) n-BuLi (60 eq), THF, -78 degrees Centigrade, 0.5 hours;
(c) B(OMe)$_3$, -78 to 0 degrees Centigrade;
(d) H$_2$O$_2$, aqueous NaOH, -78 to 25 degrees Centigrade, 40% yield (three steps);
(e) n-hexyl bromide, NaH, DMF, 70 degrees Centigrade, 24 hours, 85% yield.

Bromination of compound 2 with NBS in acetone provides tetrabromocalix[4]arene compound 3 in a 53% yield (SCHEME 2). Tetrahydroxylated 1,3-alternate derivative compound 4 was obtained through bromo-lithium exchange in compound 3 (n-BuLi, THF, at -78 degrees Centigrade), followed by treatment with B(OMe)$_3$ and oxidation with H$_2$O$_2$ and aqueous NaOH (with a 40% yield after three steps). Calixarene compound 4 was subsequently alkylated with n-hexylbromide and NaH in hot DMF to yield octa-hexyloxycalix[4]arene compound 5 (about 85% yield). Mesitylene derived 1,3-alternate compound 6 was obtained for comparison, according to known procedures (see e.g., Pappalardo, S et al. *J. Org. Chem.* 1992, 57, pp. 7102-7109 or Staffilani, M. et al. *Organometallics* 1998, 17, pp. 1732-1740) and subsequent O-alkylation with n-hexylbromide (SCHEME 3).

SCHEME 3

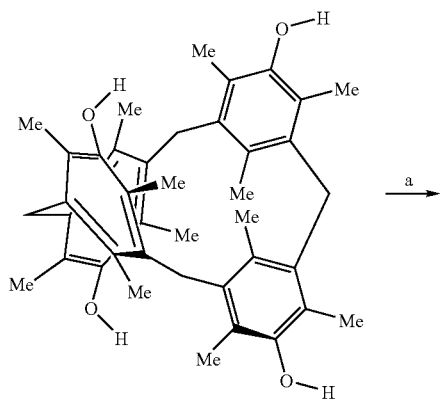

-continued

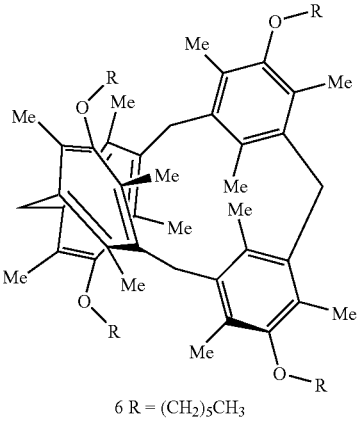

6 R = (CH$_2$)$_5$CH$_3$ (a) n-hexyl bromide, NaH, DMF, 70 degrees Centigrade, 72 hours, 50% yield.

Interaction of Calix[4]arenes with Nitrogen Oxide Compounds of the Present Invention.

Bubbling NO$_2$ through the solutions of compounds 1, 2 and 5 in CHCl$_3$ resulted in instant identification of the complex, e.g., deep coloration. For example, solutions of compound 1 and compound 5 turned blue to dark blue, and a solution of compound 2 became purple to deep purple. The UV-vis spectra changed accordingly: the broad bands appeared at $\lambda_{max}$ of about 560, 512 and 600 nm for NO$_2$-exposed solutions of compounds 1, 2 and 5, respectively. This is in contrast to the colorless solution of compounds 1, 2 and 5 and the yellow to pale yellow solution of NO$_2$ in CHCl$_3$ prior to mixing.

In the reactions with non-cyclic anisole (e.g., methoxybenzene), identification (e.g., coloration) occurred but was less pronounced upon exposure to NO$_2$. Moreover, when mesitylene-derived, Pappalardo's calixarene 6, with the sterically blocked and conformationally much more rigid cavity, was tested, the complex was not detected (e.g., no coloration was observed). In compound 6, the pair of methyl groups in the ortho-positions relative to the oxygen forces the methyl groups of the adjacent aromatic rings towards each other, not only blocking an access to the cylindrical inner cavity, but also significantly rigidifying it. The same effect takes place on the other side of the calixarene 6, which makes its interior completely blocked. These reactions show the importance of cavities in the described transformations and illustrate NO$^+$ coordination inside 1, 2 and 5.

According to the molecular modeling performed on these compounds (e.g., using MacroModel 7.1), one NO$^+$ cation can fit inside the cavities of compounds 1, 2 and 5, and neither bent NO$_2$ nor bulky NO$_3$— can be accommodated. Two parallel aromatic rings of a cone calix[4]arene participate in the NO$^+$ complexation, and all four rings of a 1,3-alternate calixarene are involved. In mesitylene derived calixarene 6, no NO$^+$ encapsulation may occur for steric reasons.

While an instant detection of a complex (e.g., nitrosated compounds 1, 2, and 5 via rapid coloration) shows charge-transfer between the prereactive nitrosating/nitrating species and the compounds (i.e., 1, 2, and 5), the actual charge-transfer itself may be difficult to monitor. Interaction of NO$_2$ with compounds 1, 2, and 5 is very dynamic, and initial $^1$H NMR analysis of the solutions showed complex, quickly changing pictures; the NO$_2$/N$_2$O$_4$ mixture is an effective nitrosating/nitrating agent. Not surprisingly, the NO$_2$-containing CHCl$_3$ solutions of compounds 1 and 2 decolored within or at about 1 to 2 hours, yielding mixtures of known p-nitrated calixarenes (preparative TLC, $^1$H NMR). Calixarene 5, much more activated for the electrophilic aromatic substitution, reacted with NO$_2$ more quickly—as quickly as within a few minutes—producing a complex mixture of dealkylated and oxidized products.

When compounds 1 and 2 are simultaneously treated with SnCl$_4$ and 2 to 3 equivalents of NO$_2$, no nitration products are detected. Precipitation with hexanes resulted in detectable solids (e.g., deeply colored, moisture sensitive), assigned to nitrosonium complexes 7 and 8 (>90% yield). These complexes are very stable and can be stored, in the absence of moisture, for about several weeks, both in CHCl$_3$ solution and in the solid state. In one embodiment, complex 7 and 8 are identified by their color, wherein complex 7 is generally a dark blue and complex 8 is generally a deep purple.

Analysis and Characterization of Compounds and Complexes of the Present Invention.

Some spectral features of the obtained nitrosonium complexes are presented in the TABLE. The UV-vis spectra showed broad charge-transfer bands at $\lambda_{max}$ of about 563 and 524 nm, and the FTIR spectra exhibited characteristic arene-NO$^+$ stretching at wavelengths of about $v$=1923 cm$^{-1}$ and 1955 cm$^{-1}$ for complexes 7 and 8, respectively. The $^1$H NMR spectra of complexes 7 and 8 exhibited new sets of the calixarene signals as well. In particular, aromatic CH protons of guest-free compound 1 were seen as a singlet at 6.76 ppm. In nitrosonium complex 7, these were transformed into a singlet at 6.99 ppm. The methylene bridge CH$_2$ protons of compound 1 were recorded as doublets at 4.41 and 3.12 ppm (J=12.5 Hz). In complex 7, these were seen as doublets at 4.39 and 3.44 ppm (J=13 Hz). The aromatic protons of free compound 2 were seen as a doublet and a triplet, 2:1, at 6.92 and 6.68 ppm, respectively (J=7.5 Hz). In nitrosonium complex 8, these were transformed into a triplet and a doublet, 1:2, at 7.17 and 7.08 ppm, respectively (J=7.5 Hz). The methylene bridge CH$_2$ and OCH$_2$ protons of compound 2 were seen as a singlet and a triplet, 1:1, at 3.62 and 3.54 (J=7.5 Hz), respectively. In complex 8, these were transformed into a singlet and a triplet, 1:1, at 3.60 and 3.87 (J=7.5 Hz), respectively. Elemental analysis of the moisture sensitive and thermally unstable complexes 7 and 8 proved to be difficult but reproducibly showed the CHN ratios corresponding to the presence of only one NO$^+$ cation in both structures.

TABLE 1

Spectroscopic data for calix[4]arenes 1, 2, and 5, and their nitrosonium complexes.

| Compound | δ, ppm | $v$, cm$^{-1}$ | $\lambda_{max}$, nm |
|---|---|---|---|
| 1 | 6.76 (s, arom), 4.41, 3.12 (2 x d, CH$_2$) | | |
| 2 | 6.92 (d, arom), 6.68 (t, arom), 3.62 (s, CH$_2$), 3.54 (t, OCH$_2$) | | |
| 5 | 6.55 (s, arom), 3.83 (t, OCH$_2$), 3.62 (s, CH$_2$), 3.35 (t, OCH$_2$) | | |
| 5•NO$^+$SbF$_6^-$ | 6.54 (s, arom), 3.93 (t, OCH$_2$), 3.76 (t, OCH$_2$), | 1876 | 600 |
| 7 | 6.99 (s, arom), 4.39, 3.44 (2 x d, CH$_2$) | 1923 | 563 |
| 8 | 7.17 (t, arom), 7.08 (d, arom), 3.87 (t, OCH$_2$) | 1955 | 524 |

At 295±1 K; The above reported spectral features of complexes 1.NO$^+$SbF$_6^-$, 2.NO$^+$SbF$_6^-$, and 5.NO$^+$SbF$_6^-$ are similar to those of complexes 7, 8, and 9, respectively; In CDCl$_3$ for $^1$H NMR and FTIR, and in CHCl$_3$ for UVvis.

Independent structural evidence came from the complexation reactions between calixarenes 1 and 2 and commercially available $NO \cdot SbF_6^-$ salt. Specifically, the $CDCl_3$ solutions of compounds 1 and 2 were treated with $NO^+SbF_6^-$ at about 295 K and the complexation induced changes in the UV-vis, FTIR and $^1H$ NMR spectra (as recorded). Under these conditions, the complexation process proved to be rather slow, however after about 20 hours no starting calixarenes 1,2 were observed and the corresponding UV-vis, FTIR and $^1H$ NMR spectra exhibited features similar to those of nitrosonium complexes 7,8.

Analogously, a nitrosonium complex of calixarene 5 was obtained. The UV-vis spectrum of the detected complex $5.NO^+SbF_6^-$ (e.g., visible as dark blue) showed broad band at about $\lambda_{max} \sim 600$ nm, and the FTIR spectrum exhibited characteristic arene-$NO^+$ stretching at about 1876 $cm^{-1}$. The $^1H$ NMR spectrum of $5.NO^+SbF_6^-$ is different from complex 5 as well. For example, the methylene bridge $CH_2$ and both $OCH_2$ protons of complex 5 were seen as a singlet and two triplets, 1:1:1, at 3.62, 3.83 (J=7 Hz), and 3.35 ppm (J=7 Hz), respectively. In complex $5.NO^+SbF_6^-$, these were observed at 3.44, 3.93 (J=7.5 Hz), and 3.76 ppm (J=7.5 Hz), respectively.

The association constants for the above complexes were too high to be measured by the $^1H$ NMR technique. Even slight excess of $NO^+SbF_6^-$ results in the complete complex formation in $CDCl_3$, and no free calixarenes 1, 2, and 5 were observed after equilibration. The $K_{ass}$ values >$10^6$ $M^{-1}$ ($\Delta G^{295}$>8 kcal $mol^{-1}$) for the complexes were estimated and in agreement with published values in $CH_2Cl_2$ (e.g., see Rathore, R. et al. Angew. Chem. Int. Ed. 2000, vol. 39, pp. 2123-2127). While complexes $1.NO^+SbF_6^-$ and $2.NO^+SbF_6^-$ formed slowly, over about 20 hrs, it took only a few minutes to form complex $5.NO^+SbF_6^-$—. Moreover, highly electrophilic $NO^+$ tended to further react with $5.NO^+SbF_6^-$, and unidentified impurities were seen in the NMR spectrum after several minutes. Unlike complexes $1.NO^+SbF_6^-$ and $2.NO^+SbF_6^-$, which are chemically stable for weeks, complex $5.NO^+SbF_6^-$-decomposed within a day (as observed by $^1H$ NMR).

Addition of $H_2O$ or MeOH to the freshly prepared $CHCl_3$ solutions of complexes 7 and 8 and the nitrosonium complexes prepared from 1, 2 and 5 and $NO^+SbF_6^-$, resulted in the complete complex dissociation and recovery of calixarenes 1, 2 and 5 (as observed by preparative TLC, UVvis, $^1H$ NMR).

Spectral data for the reactions between compounds 1 and 2 and $NO_2$, in the absence of $SnCl_4$ were re-observed. As excess $NO_2$ was passed through the solution of compound 1, nitrosonium complex $[1.NO^+]NO_3^-$ was clearly seen (UV-vis, $^1H$ NMR), along with the mixture of nitration products. For compound 2, no signals for nitrosonium complex $[2.NO^+]NO_3^-$ were detected, because, while formed, these nitrosonium species quickly react with an excess $NO_2$. Both reactions subsequently yield p-nitrated calixarenes.

As such, reactions between $NO_2/N_2O_4$ and O-alkylated calix[4]arenes proceed via the $NO^+$ encapsulation. In addition, calix[4]arene-nitrosonium complexes can be significantly stabilized by Lewis acids.

Host-Guest Dynamics of the Present Invention.

As evident from the $^1H$ NMR data, the $NO^+$ exchange in and out of the cavity is slow on the NMR time scale. For example, in the titration experiments between calixarenes 1 and 2 and $NO^+SbF_6^-$, both free and complexed species can be observed separately. This is typical for the host-guest complexes with high $K_{ass}$>$10^6$ $M^{-1}$ values. On the other hand, the $NO^+$ guest, with the van der Waals dimensions <2 Å, freely migrates within the cavity at room temperature. Indeed, the $^1H$ NMR spectra of complexes 7, 8 possess the same symmetry as guest-free calixarenes 1, 2, which in principle should be reduced upon complexation with non-symmetrical $NO^+$.

Cone calix[4]arene complex 7 should have a pinched, $C_{2v}$ symmetrical conformation, since only two opposite, cofacial aromatic rings trap $NO^+$. However, the observed at room temperature NMR spectrum exhibits a $C_{4v}$ symmetry, indicating a fast (on the NMR time scale) exchange between two $C_{2v}$ structures.

1,3-Alternate calix[4]arene complex 8 should exhibit a $C_{2v}$ symmetry, with two different top and bottom halves of the skeleton. Instead, the observed symmetry is $S_4$, with equal top and bottom halves.

In one aspect of the present invention, the complexation process is reversible, and the $NO^+$ guest can readily leave the calixarene cavity. For example, addition of $H_2O$ to the freshly prepared $CHCl_3$ solutions of complexes 7, 8 resulted in the complete dissociation and recovery of calixarenes 1, 2. Complex 8 generally decolored within seconds; complex 7 may take several minutes to decompose. Kinetics factors appears to be responsible for these observations, where t-Bu groups at the upper rim of the latter complex pose significant steric hindrances and protect the encapsulated $NO^+$ species from the entering $H_2O$. Such stability of the arene-$NO^+$ complex is without precedent.

In another aspect of the present invention, $NO^+$ guest can be transferred from one calixarene container to another. Calixarene 5 was specifically designed to promote such transfer from the preformed complex 8. Four additional, electron donating $O(CH_2)_5CH_3$ groups were introduced in p-positions to the initial set of $O(CH_2)_5CH_3$ groups. This makes cavity of compound 5 significantly more π-electron rich and dramatically increases its affinity towards positively charged $NO^+$.

Examples of the exchange include obtaining complex 8 by treating calixarene 2 with 3 equivalents $NO_2$ and 1 equivalent $SnCl_4$ in $CHCl_3$. Further, complex 8 and "empty" host 5 were mixed in an 1:1 ratio at 295 K in dry chloroform, and the UV-vis and $^1H$ NMR spectra were recorded over two hours. Due to the strong affinity of 2 towards $NO^+$, the guest presence outside the cavity, in a bulk solution, was considered negligible; the only source of $NO^+$ was complex 8. Initially, the $^1H$ NMR spectrum exhibited only sets of signals for complex 8 and free calixarene 5, and the corresponding UV-vis spectrum showed only the characteristic absorption for charge-transfer in complex 8. Within minutes, however, the guest transfer was clearly detected. The band at $\lambda_{max}$ of about 524 nm, assigned to complex 8, systematically decreased and a new band at $\lambda_{max}$ of about 600 nm, corresponding to new complex 9, appeared.

The nitrosonium transfer can be identified visually. For example, a purple solution of complex 8 in $CHCl_3$ turns blue upon addition of calixarene 5. When followed by $^1H$ NMR spectroscopy, the $NO^+$ exchange resulted in clean transformation of the spectra from mixture 8+5 to mixture 2+9. The methylene bridge $CH_2$ and $OCH_2$ protons of complex 8, seen as a singlet and a triplet, 1:1, at 3.60 and 3.87 ppm (J=7.5 Hz), may slowly decrease in intensity. Instead, two $OCH_2$ triplets at 3.93 and 3.76 ppm (J=7.5 Hz) and the methylene bridge $CH_2$ singlet at 3.44 ppm appear and grow (assigned to complex 9). Complex 9 was confirmed in a series of independent experiments between 5 and $NO^+SbF_6^-$—. Signals for "empty" calixarene 2 also appear, although slightly shifted due to the presence of $SnCl_4$, and signals for complex 8 disappear. Within about an hour the nitrosonium transfer may be completed; both the $^1H$ NMR and UV-vis spectra exhibited only the signals of complex 9 and free calixarene 2. No traces of initial complex 8 were detected.

This is a new example of a quantitative guest transfer between two different molecular containers. As such, molecular containers of the present invention serve as storage for information and processing, especially because they can be readily detected (e.g., by color changes) when the compounds are switched between two distinguishable states. In addition to switching from a free and entrapped state with the calixarene complexes of the present invention, the nitrosonium may be further transferred to another substrate (e.g., solid support, solid interface, etc. that accepts nitrosonium).

Functionalized Silica Gel of the Present Invention.

In the present invention, the interaction of calix[4]arene and a nitrosonium ion is: (a) reversible, (b) detectable (e.g., by color changes) and (c) effective for purifying $NO_x$ compounds in the presence of other gases, such as $H_2O$, $O_2$, HCl, HBr, $SO_x$, and $NH_3$. In particular, these other vapors/gases are not involved in the same interactions/reactions with calixarenes. For example, neutral NO gas does not interact with calixarenes.

Current $NO_2$ sensors are generally electrochemical and monitor changes in potential upon exposure of metal surfaces to $NO_2$. In many cases however, other vapors —$H_2O$, $O_2$, HCl, HBr, $SO_x$, and $NH_3$ significantly influence detector selectivity and therefore its sensitivity. Optical sensors, generally based on color changes in a reaction between $NO_2$ and certain organic compounds, are more selective as the reactions are specific. However, reversibility of these sensing devices is not easy to achieve.

For application in any sensing technology, receptor molecules must not only be synthetically available, but also readily immobilizable on solid supports or surfaces. A wide variety of polymers and nanomaterials are commercially available. In one embodiment of the present invention, a solid support is functionalized with calixarene modules of the present invention (e.g., 3-aminopropylated silica gel). Molecular modeling of calix[4]arene fragments (of about 10×10 Å in dimension) attached to a solid support via the lower rim indicates the proper configuration of the upper rim to sufficiently respond to the presence of and to detect a gas analyte.

Calixarenes may be successfully attached to a surface, wherein tris-O-substituted calixarene 10, prepared by selective alkylation of the parent calix[4]arene with n-hexylbromide and BaO/Ba(OH)$_2$29 in DMF (69%), was further alkylated with ethyl bromoacetate to afford derivative compound 11 ($Na_2CO_3$, MeCN, 89%). (SCHEME 4)

SCHEME 4

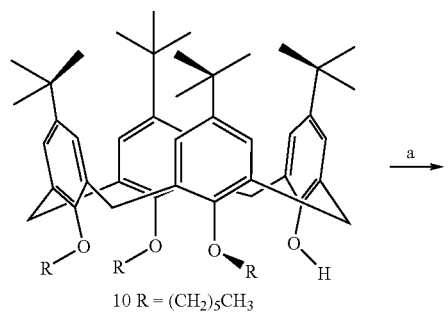

10 R = (CH$_2$)$_5$CH$_3$

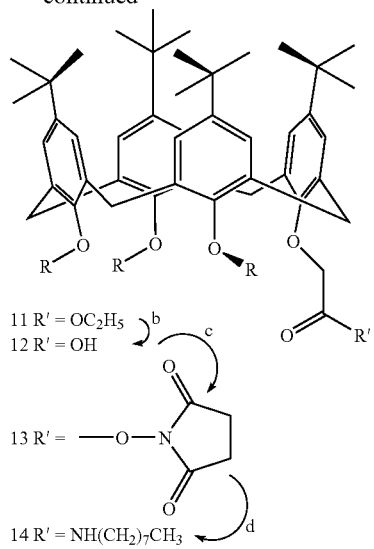

11 R' = OC$_2$H$_5$
12 R' = OH

13 R' = —O—N

14 R' = NH(CH$_2$)$_7$CH$_3$ a) BrCH$_2$C(O)OC$_2$H$_5$, Na$_2$CO$_3$, MeCN, 80 degrees Centigrade, 12 h, yield of about 89%;
(b) KOH, THF—H$_2$O, 100 degrees Centigrade, 12 h, then aqueous HCl, yield of about or >95%;
(c) N-hydroxy succinimide, DCC, DMAP, THF, room temperature, 12 hours, yield of about 83%;
(d) CH$_3$(CH$_2$)$_7$—NH$_2$, Et$_3$N, THF, room temperature, 12 hours, yield of about 65%.

As in SCHEME 4, derivative compound 11 was hydrolyzed with KOH in a THF—H$_2$O mixture, resulting in calixarene acid 12 in a quantitative yield. Acid compound 12 was further activated with N-bromosuccinimide (DCC, DMAP, THF) to afford active ester compound 13 (yield of about 83%). Compound 13 readily reacts with amines. Thus, amide 14 was prepared from compound 13 and n-octylamine (Et$_3$N, THF, yield of about 65%) and used for control experiments. Analogously, ester compound 13 was coupled to 3-aminopropyl-functionalized silica gel in THF in the presence of Et$_3$N to afford material 15. The presence of a calix[4]arene fragment in compound 15 was confirmed by the FTIR analysis in KBr disks: ν(CH) of about 2960 cm$^{-1}$ and ν(C=O) of about 1650 cm$^{-1}$ were recorded (similar to the stretching of model calixarene amide 14: ν(CH)=2964 cm$^{-1}$ and ν(C=O)=1680 cm$^{-1}$). From the CHN analysis, about 17% calixarene loading was achieved (there is steric bulkiness of the calixarene fragment).

In the $NO_2$ entrapment demonstration, a stream of the gas was passed through Pasteur pipettes, loaded with silica gel 15. In one pipette, dry silica gel 15 was loaded, and the other contained 15 preliminary wetted with CHCl$_3$. With both silica gels, entrapment of a nitric oxide compound was instantly detected (e.g., color change, such as the gel turning dark purple) and indicated the NO$^+$ complexation. When the material was wetted, the identification may be quicker and more complexation may occur (e.g., the color of the wetted material appeared to be deeper and lasted for hours). The dry material decolored within minutes. The FTIR spectrum, recorded in KBr disks, gave weak but reproducible stretch at ν of about 1920 cm$^{-1}$, indicating the presence arene-NO$^+$ complexes. No detection was apparent for the pipette loaded with the starting solid support, e.g., 3-aminopropylated silica gel. Columns were prepared by (A) loading with starting aminopropyl functionalized silica gel, (B) loading with dry silica gel 15, (C) loading with 15 and flashed with CHCl$_3$ and then flashing all three columns with $NO_2$ (about 30 seconds) followed by photographing columns about 2-3 minutes later. For the present invention, calixarene cavities play a role in the described processes. Indeed, a solid support such as silica gel 15 is applicable for $NO_2$ detection and may even be used for purification of other nitrogen oxide compounds, especially NO.

Nitrosating Reagents of the Present Invention.

In addition to the previously described features of the present invention is the ability of calixarene-nitric oxide containing molecules. complex to act as nitrosating agents.

It is known, that reactions between $NO^+$ generating agents (e.g., NOCl, $N_2O_3$, $NO_2/N_2O_4$, nitrosonium salts, etc.) and amides and short peptides proceed via N-nitrosation and yield biologically important nitroso-derivatives. Nitrosation of peptides may be used in analytical protocols, such as in protein sequencing, and occurs in biologic processes, when $NO_X$ (e.g., as atmospheric pollutants) interacts with biological tissues and fluids. Here, the corresponding reaction mechanisms typically incorporate an electrophilic attack of $NO^+$ on a nucleophilic oxygen or nitrogen of the substrate.

In yet another embodiment of the present invention, a sample such as 1,3-alternate based nitrosonium complex 8 was mixed with AlkC(O)NHMe 16a-c (Alk=n-Pr, n-Hex, n-Hept) in dry $CHCl_3$ and stirred at room temperature for several hours. The corresponding N-nitrosoamides AlkC(O)N(NO)Me (17a-c) were formed in about 30-40% yield. Under the same conditions, the cone calixarene complex 7 reacted very slow, and only traces of the N-nitrosoamide products were detected by $^1H$ NMR spectroscopy. Likewise with water, t-Bu groups at the upper rim of complex 7 impose steric hindrances and protect the encapsulated $NO^+$ species from the substrate. The rate limiting formation of the nitroso intermediates should take place within the calixarene cavity, prior to the $NO^+$ dissociation. Once formed, these sterically bulky species leave the interior, and undergo further transformations in bulk solution.

These transformations provide additional structural evidence for the calixarene-$NO^+$ complexes of the present invention and illustrate the utility of calixarenes as supramolecular/encapsulated nitrosating reagents (e.g., complexes as encapsulated reagents for nitrosation). As used herein, encapsulated reagents of the present invention are highly reactive species, reversibly entrapped within a host' cavity that may be released to the reaction mixture via one or more methods. The cavity offers protection from the bulk environment and thus controls the reaction rates. Reactions with encapsulated reagents may occur either within the cavity interior, or outside, upon release. Some of the more critical factors responsible for reagent release and for the reaction to occur are noncovalent forces holding the molecule-within-molecule complex together, such as temperature, solvent polarity and the substrate-cavity size-shape fit. Indeed, with deeper calixarenes, where the cavities could accommodate the reaction intermediates, supramolecular effects in these processes are more pronounced.

The present invention provides a new and improved $NO_X$ sensing and fixation process that employs simple calix[4] arenes. With the present invention, calixarenes provide and transmit information about $NO_X$ binding that can be readily detected (e.g., via visible light signals, electrochemical changes, spectroscopic changes), wherein the charge-transfer interactions allow the detection of various forms of nitrogen oxide compounds in the presence of other gas mixtures, such as $H_2O$, $O_2$, HCl, $SO_X$, $NH_3$, NO, as well as chemical mixtures produced by chemical processing and manufacturing. The calixarenes and complexes of the present invention may be immobilized, in solution or attached to a ligand. The resulting calixarene-nitrogen oxide compound complexes may be used as vehicles for nitrosonium transfer and encapsulated nitrosating reagents. $NO_2^-$/$NO_X$ sensing molecules and as storing materials.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A device for sensing $NO_X$ compounds comprising:
   a calix[4]arene compound, wherein the calix[4]arene compound forms a stable and reversible calix[4]arene-nitrosonium complex, wherein a detectable charge-transfer reaction occurs between at least one $NO^+$ and the calix[4]arene detectable as a color change, wherein $NO^+$ is derived from an oxide of nitrogen in a form other than nitric oxide.

2. The device of claim 1, wherein the detection is selected from the group consisting of visualization, measurement of electrochemical changes, and measurement of spectroscopic changes.

3. The device of claim 1, wherein the complex undergoes dissociation.

4. The device of claim 3, wherein the complex is decolorized.

5. The device of claim 1, wherein the calix[4]arene compound is alternatively a cone calix[4]arene, a 1,3-alternate calixarene or a combination thereof.

6. The device of claim 1, wherein the calix[4]arene compound is optionally immobilized, in solution, attached to a ligand, attached to a solid support, or any combination thereof.

7. The device of claim 1, wherein the charge-transfer reaction is detected in the presence of mixtures selected from the group consisting of $H_2O$, $O_2$, HCl, $SO_X$, $NH_3$, NO, their derivatives and combinations thereof.

8. The device of claim 1, wherein the complex is a storage device for the $NO^+$ cation.

9. The device of claim 1, wherein the complex is capable of transferring the $NO^+$ cation to a substrate.

10. The device of claim 1, wherein the complex is stabilized by one or more Lewis acids.

11. A device for purifying chemical compounds containing $NO_X$ comprising:
    a calix[4]arene compound, wherein the calix[4]arene compound reversibly forms a calix[4]arene-nitrosonium complex and purifies the chemical compound free of $NO^+$ wherein $NO^+$ is derived from an oxide of nitrogen in a form other than nitric oxide.

12. The device of claim 11, wherein the calix[4]arene compound is optionally immobilized, in solution, attached to a ligand, on a solid interface, attached to a solid support, or a combination thereof.

13. The device of claim 11, wherein the complex is a storage device for the $NO^+$ cation.

14. The device of claim 13, wherein the complex is chemically stable for at least several weeks.

15. A method of purifying chemical compounds comprising:
    exposing a calix[4]arene compound to a mixture of chemical species containing at least one $NO_X$ compound;
    allowing the calix[4]arene compound to interact with the mixture, wherein the calix[4]arene compound forms a stable and reversible calix[4]arene-nitrosonium complex with an $NO^+$ and wherein $NO^+$ is derived from an oxide of nitrogen in a form other than nitric oxide, wherein a detectable charge-transfer reaction occurs between the $NO^+$ and the calix[4]arene for identification of the $NO^+$.

16. A molecular container comprising:
a calix[4]arene compound enriched with electron donating groups; and
at least one $NO^+$, wherein $NO^+$ is derived from an oxide of nitrogen in a form other than nitric oxide, wherein the $NO^+$ is attracted to an electron donating group, forms a stable and reversible calix[4]arene-nitrosonium complex and wherein the $NO^+$ is now made available for transfer to a second container that accepts the $NO^+$.

17. The molecular container of claim 16, wherein the calix[4]arene compound complexes the $NO^+$ cation and is capable of storing it.

18. The molecular container of claim 16, wherein the calix[4]arene compound complexes the $NO^+$ cation and is capable of transferring it to another substrate.

19. The molecular container of claim 16, wherein the second container is selected from the group consisting of calix[4]arene compound, solid support, and solid interface.

20. An optical switch comprising:
a reversible and stable calix[4]arene-nitrosonium complex formed by noncovalent forces between a calix[4]arene compound and free nitrosonium in which the nitrosonium switches between a free and a complexed state wherein the switching is detected optically, wherein the nitrosonium is derived from an oxide of nitrogen in a form other than nitric oxide.

21. The optical switch of claim 20 wherein the calix[4]arene compound is immobilized on a solid support.

22. An optical switch comprising:
a means for reversibly forming a calix[4]arene-nitrosonium complex in a stable form by noncovalent forces, wherein the nitrosonium is derived from an oxide of nitrogen in a form other than nitric oxide; and
a means for detecting the presence of the complexed nitrosonium cation.

23. An improved nitrosating agent comprising:
a compound that reversibly forms a calix[4]arene-nitrosonium complex for entrapping one or more nitrosonium cations in a deep cavity by noncovalent forces and releases the one or more nitrosonium cations under reactive conditions, wherein the reactive conditions are selected from the group consisting of a change in temperature, solvent polarity, and cavity shape.

* * * * *